(12) United States Patent
Mentink et al.

(10) Patent No.: US 12,029,806 B2
(45) Date of Patent: Jul. 9, 2024

(54) TOPICAL COMPOSITION FOR TREATING BAD BODY ODORS, IN PARTICULAR HALITOSIS

(71) Applicant: ROQUETTE FRERES, Lestrem (FR)

(72) Inventors: Léon Mentink, Lille (FR); Daniel Wils, Morbecque (FR); Géraldine Louvet-Pommier, Lachelle (FR); Sophie Piot, Paris (FR)

(73) Assignee: Roquette Freres, Lestrem (FR)

( * ) Notice: Subject to any disclaimer, the term of this patent is extended or adjusted under 35 U.S.C. 154(b) by 122 days.

(21) Appl. No.: 17/593,730

(22) PCT Filed: Mar. 27, 2020

(86) PCT No.: PCT/EP2020/058679
§ 371 (c)(1),
(2) Date: Sep. 23, 2021

(87) PCT Pub. No.: WO2020/193743
PCT Pub. Date: Oct. 1, 2020

(65) Prior Publication Data
US 2022/0192962 A1    Jun. 23, 2022

(30) Foreign Application Priority Data
Mar. 28, 2019 (FR) ..................................... 1903283

(51) Int. Cl.
| | | |
|---|---|---|
| *A61K 8/73* | (2006.01) | |
| *A61K 8/49* | (2006.01) | |
| *A61Q 11/00* | (2006.01) | |
| *A61Q 15/00* | (2006.01) | |

(52) U.S. Cl.
CPC ............ *A61K 8/738* (2013.01); *A61K 8/4973* (2013.01); *A61Q 11/00* (2013.01); *A61Q 15/00* (2013.01)

(58) Field of Classification Search
CPC ... A61K 8/20; A61K 8/00; A61K 8/18; A61K 38/47; A61K 47/12; A61K 47/26; A61Q 11/00
USPC .......................... 424/49, 401, 78.03, 488, 65
See application file for complete search history.

(56) References Cited

U.S. PATENT DOCUMENTS

| | | | |
|---|---|---|---|
| 4,267,166 A | | 5/1981 | Yajima |
| 5,360,899 A | * | 11/1994 | Nussstein ................ B01J 20/26 536/4.1 |
| 6,001,341 A | * | 12/1999 | Genova .................... A61K 8/37 424/76.8 |
| 6,123,932 A | * | 9/2000 | Guskey .................. A61K 8/738 424/405 |
| 8,258,123 B2 | | 9/2012 | Windisch |
| 2018/0271765 A1 | | 9/2018 | Gontarz |

FOREIGN PATENT DOCUMENTS

| | | | | |
|---|---|---|---|---|
| CN | 109289042 | * | 2/2019 | ............. A61K 38/47 |
| DE | 102006057047 A1 | | 6/2008 | |
| EP | 2839828 A1 | * | 2/2015 | ............. A61K 31/34 |
| JP | 2007169228 A | | 7/2007 | |
| JP | 2017095356 A | | 6/2017 | |
| WO | 9522960 A1 | | 8/1995 | |
| WO | 9817239 A1 | | 4/1998 | |
| WO | 0030600 A1 | | 6/2000 | |
| WO | 2008064948 A1 | | 6/2008 | |
| WO | WO-2009018069 A2 | * | 2/2009 | ........... A61K 31/715 |
| WO | 2013045330 A2 | | 4/2013 | |
| WO | 2017106467 A1 | | 6/2017 | |
| WO | 2019106316 A1 | | 6/2019 | |

OTHER PUBLICATIONS

The English translation of the International Search Report and Written Opinion, mailed on Apr. 24, 2020, in the corresponding PCT Appl. No. PCT/EP2020/058679.
Grain and Oil Food Technology, edited by ZHAO Ping, Chapter 6 Modified Starch, Lanzhou: Gansu Science and Technology Publishing House, Nov. 2004.

* cited by examiner

*Primary Examiner* — Walter E Webb

(57) ABSTRACT

The present application pertains to the field of cosmetics, more specifically the field of topical care of bad odors, by the action of a bactericidal and/or bacteriostatic topical composition, and of capturing odors. The topical composition according to the invention comprises at least one cyclodextrin, a 1,4-3, 6-dianhydrohexitol and/or a 1,4-3, 6-dianhydrohexitol derivative. It can be useful for the oral sphere, but also for areas of the skin where bad odors may develop due to microbial activity, namely the underarms, crotch and feet. Preferably, the topical composition of the invention is used for treating the oral sphere, most preferably for treating halitosis.

14 Claims, No Drawings

TOPICAL COMPOSITION FOR TREATING BAD BODY ODORS, IN PARTICULAR HALITOSIS

TECHNICAL FIELD

The present application pertains to the field of cosmetics, more specifically in the field of topical care of bad odors, by the action of a bactericidal and/or bacteriostatic topical composition, and of capturing odors. The composition according to the invention can be useful for the oral sphere, but also for areas of the skin where bad odors may develop due to microbial activity, namely the underarms, crotch and feet. Preferably, the topical composition of the invention is used for treating the oral sphere, more preferably for treating halitosis.

BACKGROUND ART

In patent PCT/FR2018/053059, the applicant proposes using dianhydrohexitols, in particular isosorbide, to eliminate bad bacteria from the oral microbiome. The effects attributed to this removal are a reduction in dental plaque, a reduction in gum damage, and a reduction in demineralization of the teeth. No mention is made as to the bad odors developed due to the microbial activity of the bacteria eliminated by the invention of this application.

In U.S. Pat. No. 4,267,166 by Yajima, a method for treating bad odors in human breath is based on the use of cyclodextrin in an edible composition. This composition does not comprise any dianhydrohexitol.

Application WO 2008 064948 from Henkel discloses a mouthwash solution comprising water, ethanol and at least one cyclodextrin. The mouthwash solution can also comprise polyhydric alcohols such as in particular the two polyols that xylitol and sorbitol are. The more specific category of polyhydric alcohols that is the dianhydrohexitols, and, a fortiori, isosorbide, is not mentioned in this patent. In this mouthwash solution, the presence of ethanol tends to dry out the mouth, and is aggressive to the oral mucous membranes.

According to the previous documents, the use of cyclodextrins to capture bad odors is known, and the use of hexides, such as anhydrohexitols and dianhydrohexitols, is known to suppress bacteria from the oral or cutaneous microbiome, or to limit development thereof. However, use of all these molecules in a topical composition is not known, and a fortiori, use of these two types of molecules simultaneously is not known, or to combine their effects, to prevent, reduce or eliminate bad body odors, especially oral or skin odors.

No document in the state of the art propose the combination of at least one dianhydrohexitol, and at least one cyclodextrin, in a topical composition, and none encourages doing so in order to maximize the treatment of bad body odors, neither skin nor oral, much less to treat halitosis with such a composition.

The common treatment for halitosis is the use of chlorhexidine, as a bactericide, most often in mouthwashes. This substance has the major shortcomings of increasing the formation of dental plaque, inducing staining of the surface of the teeth, and also altering the taste.

TECHNICAL PROBLEM

The aim is to find a topical composition having an "anti-odor" effect, suitable for use on the whole human body, preferentially in the oral sphere, and in particular an alternative to current treatments for halitosis, which is also simultaneously:
- of natural origin,
- alcohol-free, and optionally without synthetic preservatives, so as not to irritate or attack the skin or the mucous membranes, but which could on the contrary advantageously hydrate it,
- beneficial for the microbiome, in particular the oral microbiome, namely promoting or maintaining a balanced and healthy oral microbial flora,
- and that reduces or eliminates bad odors from the first moments after its application,
- and which durably reduces the formation of bad odors, in particular which reduces the microbial strains responsible for the production of malodorous molecules.

DESCRIPTION OF EMBODIMENTS

The object of the invention is a topical, aqueous or solid composition, comprising:
- at least one native or modified cyclodextrin selected from alpha-cyclodextrins, beta-cyclodextrins, gamma-cyclodextrins, preferentially beta-cyclodextrins,
- at least one 1,4-3,6-dianhydrohexitol, selected from isosorbide, isomannide, isoidide, preferentially isosorbide, and/or at least one 1,4-3,6-dianhydrohexitol derivative.

A second object of the invention is the non-therapeutic cosmetic use of the topical composition according to the invention as an anti-odor agent in a cosmetic or dermatological preparation.

A third object of the invention relates to the topical composition according to the invention for its use in treating bad body odors.

In particular, the invention relates to a topical composition as described above or its use according to the invention for preventing, reducing or eliminating bad body odors. These bad odors can be localized on the epidermis, particularly in the armpits, crotches and feet or are in the oral sphere, for example caused by halitosis. In particular, the non-therapeutic cosmetic use of the topical composition according to the invention is made to combat, that is to prevent, reduce or eliminate, halitosis, preferentially to simultaneously combat the causes and the effects of halitosis.

Thus, according to a preferred embodiment, the invention relates to a topical composition as described above for its use in treating halitosis.

A fourth object of the invention relates to a cosmetic or dermatological preparation comprising a topical composition as described above. Preferentially, for the oral sphere, said preparation will be in the form of an oral spray, a mouthwash lotion, an oral rinsing lotion, a toothpaste, an oral tablet, an orodispersible film. Preferentially for the cutaneous sphere, said preparation will be in the form of a deodorant stick, deodorant spray, deodorant roll-on, a deodorant mask.

Anti-Odors

By "anti-odors", the Applicant means that the composition according to the invention has the ability to neutralize odors, and also the ability to prevent the formation of odors, in particular bad odors, preferentially those originating from bacterial activity of a topical microbiome, in particular human topical microbiome, and especially human oral microbiome.

Cyclodextrin

In the present application, the term "cyclodextrin" denotes and includes any one of the otherwise known cyclodextrins, such as native and unsubstituted cyclodextrins containing from 6 to 12 glucose units bonded by covalent bonds between carbons 1 and 4, and particularly alpha-, beta- and gamma-cyclodextrins containing respectively 6, 7 and 8 glucose units. The CAS numbers for these cyclodextrins are 10016-20-3 for alpha, 7585-39-9 for beta, and 17465-86-0 for gamma.

"Modified cyclodextrins" are cyclodextrins in which at least part of the OH hydroxyl groups has been converted into OR groups, where R generally denotes an alkyl or carboxyalkyl group. From this point of view, the cyclodextrin derivatives include in particular cyclodextrins substituted with an alkyl group such as methylated or ethylated cyclodextrins, but also those substituted with a hydroxyalkyl group such as hydroxypropylated and hydroxyethylated cyclodextrins, and those substituted with a carboxyalkyl group, such as carboxymethylated cyclodextrins or mixtures thereof.

Due to their completely natural origin, the preferred cyclodextrins according to the present invention are native alpha-, beta- and gamma-cyclodextrins, that is unmodified cyclodextrins. According to a preferred embodiment, the cyclodextrin used in the topical composition according to the invention is a beta-cyclodextrin, preferably "native" (not chemically modified).

However, if the solubility of the native cyclodextrin is not high enough for the topical composition or for the cosmetic or dermatological preparation, then cyclodextrins, preferentially modified beta-cyclodextrins will be preferred, preferentially hydroxyalkylated cyclodextrins, and most preferentially hydroxyalkylated beta-cyclodextrins. Even more preferentially, hydroxypropylated cyclodextrins, and most preferentially hydroxypropylated beta-cyclodextrins. Hydroxypropylated cyclodextrins that are useful in the invention have a degree of substitution, denoted by DS, with respect to hydroxypropyl ranging from 0.1 to 3, preferentially from 0.5 to 2, and most preferentially from 1 to 1.5.

When the topical composition is in solid form, the cyclodextrin may be in the form of a crystalline, pseudo-crystalline or amorphous powder.

The cyclodextrin may be in a form referred to as "free," i.e. a form in which its cavity is empty, or in the known form of inclusion complex capable of disassociating. The cyclodextrin is preferentially in a free form.

Dianhydrohexitol 1,4-3,6-dianhydrohexitol is selected from isosorbide, which is 1,4-3,6-dianhydrosorbitol, isomannide, which is 1,4-3,6 dianhydromannitol, isoidide, which is 1,4-3,6-dianhydroiditol, and mixtures of at least two of these products. Preferably, it is isosorbide, whose IUPAC name is (3R,3aR,6S,6aR)-hexahydrofuro[3,2-b]furan-3,6-diol.

The 1,4: 3,6 dianhydrohexitols, also simply called dianhydrohexitols or isohexides, are products of double internal dehydration of C6 polyols (hexitols) such as sorbitol, mannitol and iditol. In this regard, the Applicant indicates that the production of dianhydrohexitols generally generates water during their synthesis; by recovering said dianhydrohexitol in this reaction medium, a 1,4: 3,6 dianhydrohexitol is immediately available in the form of an aqueous solution of dianhydrohexitol for use according to the invention. The solutions of dianhydrohexitols can in particular be obtained according to the methods described in the aforementioned patent applications EP 1 287 000 and WO 03/043959. It is possible to choose to keep all or part of the water used during the preparation of the dianhydrohexitol or to completely eliminate the water to obtain a product in solid form that will be reverted into aqueous solution by simply adding water, which is another possibility for preparing an aqueous solution of dianhydrohexitol that can be used according to the invention.

Dianhydrohexitol Derivatives

The topical composition according to the invention can comprise at least one dianhydrohexitol derivative.

In the present application, the term "1,4:3,6 dianhydrohexitol derivative" includes all products obtained by chemical or enzymatic modification of 1,4: 3.6 dianhydrohexitol. According to one embodiment, the 1.4: 3,6 dianhydrohexitol derivative is selected from 1,4: 3,6 dianhydrohexitols esterified on one or on both hydroxyl functions (mono-ester and di-ester will be addressed respectively), the 1,4:3,6 dianhydrohexitols etherified on one or on both hydroxyl functions (mono-ether and di-ether will be addressed respectively). According to one embodiment, the 1.4: 3,6 dianhydrohexitol derivative is selected from monomethylisosorbide, dimethylisosorbide, isosorbide laurate, isosorbide oleate, isosorbide dicaprylate, isosorbide dicaprate, isosorbide dioleate, isosorbide dilinoleate, and isosorbide dilinolenate.

Alpha-Hydroxy Acid or Poly-Hydroxy Acid

According to a preferred embodiment of the invention, the topical composition comprises at least one alpha-hydroxy acid or poly-hydroxy acid or alpha-hydroxy acid or poly-hydroxy acid precursor, for example of the lactone type, preferentially a cyclic lactone such as gluconolactone, most preferentially glucono-delta-lactone.

Alpha-hydroxy acids, also known by the acronym AHA, are carboxylic acids having a hydroxyl function in the "alpha" position with respect to the acid function, on their main carbon chain, that is to say a hydroxyl function carried by a carbon atom adjacent to the carbon atom carrying the acid function. The AHAs useful in the invention are selected from glycolic acid, malic acid, lactic acid, citric acid, tartaric acid, gluconic acid.

According to one embodiment of the topical composition according to the invention, said topical composition is in liquid form, and comprises an alpha-hydroxy acid selected from glycolic acid, malic acid, lactic acid, citric acid, tartaric acid, gluconic acid, preferentially is gluconic acid.

Poly-hydroxy acids, also known by the acronym PHA, are carboxylic acids having at least two hydroxyl functions carried by adjacent carbons or spaced apart by at least one carbon atom, relative to the carbon atom carrying the carboxylic acid function. PHAs can be linear, branched, or cyclic molecules. The PHAs useful for forming the anti-odor composition of the invention are selected from gluconic acid and glucuronic acid.

Alpha-Hydroxy Acid or Poly-Hydroxy Acid Precursor

By "precursor" of alpha-hydroxy acid or of poly-hydroxy acid, the Applicant means organic molecules comprising a chemical function capable of dissociating, for example by hydrolysis in aqueous solution, and thus of forming, by chemical equilibrium of dissociation, a molecule having a carboxylic acid function having at least one hydroxyl in the alpha position, in the case of an AHA precursor, or further from the carboxylic acid function on the carbon chain, in the case of a PHA precursor.

According to one embodiment, the alpha-hydroxy acid precursor is gluconolactone. Gluconolactone, with IUPAC name (3R,4S,5S,6R)-3,4,5-trihydroxy-6-(hydroxymethyl) tetrahydro-2H-pyran-2-one, is the cyclic ester of gluconic acid. It is also called glucono-delta-lactone.

According to one embodiment of the topical composition according to the invention, said topical composition is in solid form, and comprises an alpha-hydroxy acid or poly-hydroxy acid precursor selected from lactones, preferentially from gluconolactones, and most preferentially from glucono-delta-lactone.

Complementary Polyol

According to one embodiment, the aqueous composition additionally comprises at least one linear polyol, selected from glycerol, hydrogenated glucose syrups, maltitol, mannitol, sorbitol, erythritol, isomalt, lactitol, xylitol, and preferentially selected from xylitol, maltitol and sorbitol, and very preferentially selected from xylitol and maltitol.

Physical Form of the Composition According to the Invention

The topical anti-odor composition according to the invention can be in solid form, such as a powder or scales, or in fluid form, such as a paste, a gel, or a solution. In the case of a solid form, the topical anti-odor composition is not necessarily totally anhydrous and may therefore contain water in small quantity, in particular up to about 5% by weight. In the case of a fluid form, it may be a paste, a gel or an aqueous solution having a dry matter that may be between 1 and 95% by weight. Preferably, for reasons of logistical and storage costs but also for ease of use during the production of the cosmetic or dermatological preparation for topical use, a concentrated solution, that is having dry matter greater than 30% by weight, preferentially greater than 50% by weight and better still greater than 70% by weight will rather be retained. In particular, a topical composition can be used having dry matter of between 75% and 85% by weight.

Mass Contents of Components of the Topical Composition

According to one embodiment, the topical composition according to the invention has:
- a mass content of native or modified cyclodextrin from 0.1% to 15%,
- a mass content of 1,4-3,6-dianhydrohexitol or 1,4-3,6-dianhydrohexitol derivative, from 0.1% to 25%,
- a water content ranging from 0.5% to 95%, preferentially from 1% to 95%, more preferentially from 10% to 95%, and most preferentially from 25% to 95%.

According to another embodiment, the topical composition according to the invention has:
- a mass content of native or modified cyclodextrin from 0.1% to 15%,
- a mass content of 1,4-3,6-dianhydrohexitol or 1,4-3,6-dianhydrohexitol derivative, from 0.1% to 25%,
- a mass content of alpha-hydroxy acid or poly-hydroxy acid or alpha-hydroxy acid or poly-hydroxy acid precursor, from 0.01% to 10%,
- a water content ranging from 0.5% to 95%, preferentially from 1% to 95%, more preferentially from 10% to 95%, and most preferentially from 25% to 95%.

According to another embodiment, the topical composition according to the invention has:
- a mass content of cyclodextrin or modified from 0.1% to 15%,
- a mass content of 1,4-3,6-dianhydrohexitol or 1,4-3,6-dianhydrohexitol derivative from 0.1% to 25%,
- a mass content of alpha-hydroxy acid or poly-hydroxy acid or alpha-hydroxy acid or poly-hydroxy acid precursor, from 0.01% to 10%,
- a mass content of linear polyol, selected from sorbitol, mannitol, xylitol, erythritol, ranging from 0.1% to 25%,
- a water content ranging from 0.5% to 95%, preferentially from 1% to 95%, more preferentially from 10% to 95%, and most preferentially from 25% to 95%.

Cosmetic or Dermatological Preparation

Within the meaning of the present invention, the term "cosmetic or dermatological preparation" means any cosmetic or dermatological preparation intended to be brought into contact with the skin, human or animal. Non-limiting examples of preparations for topical use comprise lotions, creams, serums, gels, ointments, balms, liquid soaps or shower gels, shampoos, foams, foundations, antiperspirants and deodorants. According to one embodiment, the cosmetic or dermatological preparation comprising the topical composition according to the invention is in the form of an oral spray, a mouthwash lotion, an oral rinsing lotion, a toothpaste, an oral tablet, an orodispersible film, a deodorant stick, a deodorant spray.

These preparations may comprise, in addition to the topical composition according to the invention, other ingredients usually used in preparations for topical use, such as for example cosmetic or dermatological active ingredients, and adjuvants such as preservatives, solubilizers or perfumes. It can also include moisturizers such as betaine, glycerin or acetamidoethoxyethanol or other active products or products with sensory effects vis-à-vis the skin, such as starch, for example.

Technical Effects

The cosmetic or dermatological preparations comprising the anti-odor composition according to the invention make it possible to eliminate the bad odors already present on the body before application, and to keep the treated part of the body odorless, or weakly odorous. When the topical composition according to the invention is used in a cosmetic preparation for oral care or hygiene, it enables instant deodorization, and a reduction or inhibition of the development of microorganisms of the oral microbiome, in particular bacteria, which reduces or prevents the formation of bad odors due to the biological activities of these bacteria. The topical composition according to the invention makes it possible to help keep breath fresh throughout the day, preferentially for a period of more than one hour.

The topical anti-odor composition according to the invention can inhibit the activity, and/or the development, of bacteria of the oral flora, and simultaneously capture the bad odors already present in the mouth. It thus acts both on the cause of bad odors, and on bad odors themselves, without any delay between these two means of action. This thus allows cosmetic preparations containing it to have an instant beneficial effect, through cyclodextrin, and a long-term effect, through 1,4-3,6-dianhydrohexitol and/or the 1,4-3,6-dianhydrohexitol derivative.

The topical anti-odor composition according to the invention has a rapid bactericidal and/or bacteriostatic effect, in particular antibacterial and/or antifungal, and can thus reduce or eliminate the presence of microorganisms of the mouth involved in halitosis, and thus maintain a fresh breath for a long time, typically several hours. In addition, the topical composition according to the invention has a moderate to strong decontaminating activity, does not induce irritation, and guarantees comfort of use.

A film-forming polymer can be advantageously added to the topical composition according to the invention, in order to develop a film on the surface of the skin or of the mucous membranes of the oral cavity, in or on which the active composition according to the invention may persist and continue to act in treating halitosis. Such polymers can be, for example, synthetic polymers such as polyvinylamines, polyvinylpyrrolidones, styrene acrylates, or preferentially polymers of natural origin, such as cellulose or starch derivatives, for example.

Uses of the Topical Composition According to the Invention

The invention also relates to the non-therapeutic cosmetic use of a topical composition according to the invention, as an anti-odor agent in a cosmetic or dermatological preparation.

The invention also relates to the topical composition according to the invention for its use in treating bad body odors, preferentially in treating halitosis.

According to one embodiment, the topical composition according to the invention or its use according to the invention makes it possible to prevent, reduce or eliminate bad body odors. These bad odors can be localized on the epidermis, particularly at the armpits, crotches and feet, or they can be localized in the oral sphere.

According to one variant, the non-therapeutic cosmetic use of the topical composition makes it possible to combat halitosis, preferentially to simultaneously combat the causes of halitosis and the effects of halitosis.

EXAMPLES

Example 1: Preparation of an Anti-Halitosis Aqueous Solution

A topical anti-odor composition according to the invention is prepared in the form of an aqueous solution, according to the composition by mass in Table 1 below, by following the protocol below.

TABLE 1

Composition of an aqueous solution according to the invention

| Phase | INCI name | Trade name | % |
|---|---|---|---|
| Phase A | Aqua | Demineralized water | qsp 100 |
| | Isosorbide | Beauté by Roquette PO500 (Roquette) | 5.00 |
| | Xylitol | Beauté by Roquette PO370 (Roquette) | 10.00 |
| | Sorbitol | Beauté by Roquette PO160 (Roquette) | 10.00 |
| | Hydroxypropyl cyclodextrin | Beauté by Roquette CD100 (Roquette) | 1.00 |
| | Mint flavor | Mint powder flavor code 023C301 (Colin Ingredients) | 1.00 |
| Phase B | Sodium benzoate | Microcare NB (Thor) | 0.50 |
| | Potassium benzoate | Microcare KS (Thor) | 0.50 |
| Phase C | Cl 42090 | FDC Blue 1 (Sensient Cosmetic Technologies) | qs |
| Phase D | Gluconolactone | Beauté by Roquette GA290 (Roquette) | Qs pH 5.8 |

As a first step, phase A is prepared. At approximately 22° C., the xylitol powder (Beauté by Roquette® P0370, from Roquette®) is dissolved in water and the sorbitol powder (Beauté by Roquette® P0160, from Roquette®) is dissolved in a volume of water approximately equal to half the volume of solution to be prepared, while stirring with a deflocculating paddle. The hydroxypropylated cyclodextrin powder (Beaute by Roquette® CD110, from Roquette®), and the aqueous isosorbide solution (Polysorb® LP, from Roquette®) are then added, successively, while waiting for complete dissolution between the two, with gentle stirring with the deflocculator blade. Then, a mint flavor is added (powdered mint flavor 023C301 from Colin Ingredients®).

Optionally, phase B can then be added, consisting of potassium sorbate (Microcare KS from Thor©) and sodium benzoate (Microcare NB from Thor©), into phase A, but these preservatives are not essential to the invention. They only serve to ensure microbiological stability.

Optionally, a dye can also be added to the solution obtained above, which for example here, is blue dye "CI 42090" sold under the trade reference "FDC Blue 1" by Sensient Cosmetic Technologies.

The preparation is completed by adding an aqueous solution of 10% m in gluconolactone (phase D) in a metered manner until a pH of 5.8 is reached. Gluconolactone is supplied by Roquette, under the trade reference Beaute by Roquette® GA290.

The invention claimed is:

1. A method for treating, preventing, reducing or eliminating bad body odors to a subject in need thereof, comprising the step of administering a composition comprising an anti-odor agent to said subject and thereby treating, preventing or eliminating bad body odors, and wherein the anti-odor agent comprises:
at least one modified cyclodextrin selected from hydroxypropylated alpha-cyclodextrins, hydroxypropylated beta-cyclodextrins, hydroxypropylated gamma-cyclodextrins, and
isosorbide.

2. The method according to claim 1 wherein the bad odors are on the epidermis.

3. The method according to claim 1 wherein the bad odors are at the underarms, crotches and feet, or are in the oral sphere.

4. The method according to claim 3 wherein the bad odors in the oral sphere are caused by halitosis.

5. The method according to claim 1, wherein the hydroxypropylated cyclodextrin has a degree of hydroxypropyl substitution from 0.1 to 3.

6. The method according to claim 1, wherein the hydroxypropylated cyclodextrin has a degree of hydroxypropyl substitution from 0.5 to 2.

7. The method according to claim 1, wherein the hydroxypropylated cyclodextrin has a degree of hydroxypropyl substitution from 1 to 1.5.

8. The method according to claim 1, wherein the modified cyclodextrin is a hydroxypropylated beta-cyclodextrin.

9. The method according to claim 1 wherein the composition further comprises at least one 1,4-3,6-dianhydrohexitol derivative selected from mono- or di-ethers of 1,4-3,6-dianhydrohexitol, or from mono- or di-esters of 1,4-3,6-dianhydrohexitol.

10. The method according to claim 1, wherein the mass content of isosorbide is from 0.1% to 25% by weight, relative to the total weight of the composition.

11. The method according to claim 1, wherein the water content ranging is from 0.5% to 95, relative to the total weight of the composition.

12. The method according to claim 1, wherein:
the mass content of modified cyclodextrin is from 0.1% to 15% by weight, relative to the total weight of the composition,
the mass content of isosorbide is from 0.1% to 25% by weight, relative to the total weight of the composition,
the water content ranging is from 0.5% to 95, relative to the total weight of the composition.

13. The method according to claim 1 wherein the composition is comprised into a cosmetic or dermatological preparation.

14. The method according to claim 13, the cosmetic or the dermatological preparation is in the form of an oral spray, a mouthwash lotion, an oral rinsing lotion, a toothpaste, an oral tablet, an orodispersible film, a deodorant stick, a deodorant spray.

\* \* \* \* \*